(12) United States Patent
Nadanami et al.

(10) Patent No.: US 6,764,582 B2
(45) Date of Patent: Jul. 20, 2004

(54) HYDROGEN SENSOR

(75) Inventors: Norihiko Nadanami, Aichi (JP); Shoji Kitanoya, Aichi (JP); Tomonori Kondo, Aichi (JP); Masaya Watanabe, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/290,162

(22) Filed: Nov. 8, 2002

(65) Prior Publication Data

US 2003/0089604 A1 May 15, 2003

(30) Foreign Application Priority Data

Nov. 9, 2001 (JP) ........................................ 2001-344780

(51) Int. Cl.$^7$ ............................................. G01N 27/407
(52) U.S. Cl. ........................ 204/424; 204/425; 204/432
(58) Field of Search ................................ 204/412, 415, 204/421–429, 431, 432

(56) References Cited

U.S. PATENT DOCUMENTS 4,824,528 A    4/1989  Polak et al.
5,322,602 A    6/1994  Razaq
5,672,811 A  * 9/1997  Kato et al.

FOREIGN PATENT DOCUMENTS

| EP | 0 862 056    | 9/1998  |
| EP | 0 911 629    | 4/1999  |
| EP | 1 103 807 A2 | 5/2001  |
| EP | 1 249 701    | 10/2002 |

OTHER PUBLICATIONS

European Search Report for EP 02 25 7763 dated Feb. 20, 2003.

* cited by examiner

*Primary Examiner*—Kaj K. Olsen
(74) *Attorney, Agent, or Firm*—Sughrue Mion, PLLC

(57) ABSTRACT

A gas sensor suitable for measuring hydrogen concentration, including a proton conductive layer (1); a first electrode (3) and a second electrode (5) provided on the proton conductive layer (1); a gas diffusion-limiting inlet (19) provided between the first electrode (3) and a measurement gas atmosphere (6) containing hydrogen gas; and a gas diffusion-limiting outlet (21) provided between the second electrode (5) and the atmosphere (6); wherein the ratio (a/b) between the diffusion resistance (a) of the diffusion limiting portion (19) and the diffusion resistance (b) of the gas outlet portion (21) is not greater than 2.

8 Claims, 3 Drawing Sheets

PRIOR ART

HYDROGEN SENSOR

BACKGROUND OF THE INVENTION

1. Field of the Invention

The present invention relates to a gas sensor including a hydrogen sensor for measuring or detecting a hydrogen component in a gas of interest, in particular, to a hydrogen sensor for measuring concentration of hydrogen contained in a fuel gas for use in a fuel cell.

2. Description of the Related Art

In response to concerns about global environmental pollution, in recent years intensive studies have been conducted on fuel cells for use as high-efficiency, clean power sources. Among such fuel cells, a polymer electrolyte fuel cell (PEFC) shows promise for automobile use and household use, by virtue of its inherent advantages, such as operation at low temperature and high output density.

A promising fuel gas for use in PEFC is a reformed gas. In this connection, in order to enhance efficiency and the like factor, a sensor capable of directly detecting hydrogen in a reformed gas must be provided. Since this sensor is used in a hydrogen rich atmosphere, an operating temperature thereof must be low (about 100° C. or lower).

Such low-temperature operation type sensor is proposed in, for example, European Patent No. 1103807A2. As shown in FIG. 5, the proposed sensor employs a proton conductive layer 101 formed from a polymer electrolyte and is configured such that a first electrode 102 and a second electrode 103 are disposed on the corresponding surfaces of the proton conductive layer 101, and the resultant assembly is held between a pair of support elements 104 and 105.

In the above-mentioned sensor, an upper support 104 includes a diffusion limiting portion 106 for diffusion of gas while establishing communication between the first electrode 102 and an outside atmosphere containing a gas to be measured, and the other support 105 includes a gas outlet portion 107 for releasing hydrogen from the sensor while establishing communication between the atmosphere and the second electrode 103. The hydrogen concentration can be measured on the basis of the limiting current flowing between the first and second electrodes 102,103.

3. Problems Solved by the Invention

However, the inventors have found a drawback that under certain conditions, the above mentioned conventional sensor has generated an undesirable output. Specifically, an abruptly varying concentration of hydrogen gas has caused transient generation of unusual electromotive force (or rather, undesired undershooting current) between the first electrode 102 and the second electrode 103, as shown in FIG. 2. As a result, during the transition, it is difficult or rather impossible to use the sensor for measuring hydrogen gas concentration.

SUMMARY OF THE INVENTION

The present invention has been achieved in order to solve the above-mentioned problem of the prior art, and an object of the present invention is to provide an improved hydrogen sensor capable of accurately measuring gas concentration even during transition.

A hydrogen sensor according to the present invention has the following major feature. That is, a gas diffusion-limiting outlet (21) provided between a second electrode (5) and a measurement gas (6) has a predetermined gas diffusion resistance which limits diffusion of hydrogen molecules entering or draining out through the outlet, when a voltage is applied across the first electrode (3) and the second electrode (5) as shown in FIG. 1. The gas diffusion-limiting outlet (21) may be formed in a support element (9) that supports a proton conductive layer (1) and encapsulates the second electrode formed on the proton conduction layer (1).

Specifically, the diffusion resistance (b) of the gas diffusion outlet (21) is so predetermined that a ratio (a/b) of the gas diffusion resistance (a) of the gas diffusion-limiting inlet (19) to the gas diffusion resistance (b) of the gas diffusion-limiting outlet (21) is not greater than 2. In other words, the gas diffusion-limiting inlet (19) is designed to have a diffusion resistance (a) of not more than two times the diffusion resistance (b) of the gas diffusion-limiting outlet (21).

More specifically, the ratio (a/b) that is the gas diffusion resistance (a) of the gas diffusion-limiting inlet (19) to the gas diffusion resistance (b) of the gas diffusion-limiting outlet (5) is from 1 to 2.

With the above feature incorporated into the hydrogen sensor, the problem of undershooting current is effectively or completely suppressed. When the diffusion resistance ratio (a/b) falls within the above range, even upon abrupt increase in the hydrogen concentration of the measurement gas, the amount of the hydrogen gas which reaches the second electrode (5) through the gas diffusion limiting outlet (21) can be rendered closer to that of the hydrogen gas which reaches the first electrode (3) through the diffusion limiting inlet (19), whereby generation of unusual electromotive force or undershooting current can be effectively suppressed. The unusual electromotive force or undershooting current herein means more than 10% of the value thereof produced from the value that correctly represents the concentration, resulting in a measurement error.

In short, the hydrogen gas entering and/or draining out of the sensor according to the present invention is effectively and stably controlled by the two diffusion resistances having close values formed respectively in the first and second support elements (3,5), one formed at the diffusion limiting inlet (19) and the other at the diffusion limiting outlet (21), whereby accurate concentration measurement of hydrogen gas contained in a hydrogen-component varying atmosphere is attained.

The present invention is applicable to both a hydrogen sensor having no reference electrode as shown in FIG. 1 and a hydrogen sensor having a reference electrode (37) as shown in FIG. 4. In the latter sensor, the voltage applied across the first and second electrodes (33,35) for measuring the limiting current that flows between the first and second electrodes (33,35) is varied while the voltage applied across the first electrode (33) and the reference electrode (37) is maintained constant, so that a wider range of the limiting current (resulting in a wider range of the hydrogen concentration) is attained, compared to the hydrogen sensor without a reference electrode.

In designing the diffusion resistance ratio (a/b) to fall in the range of 1–2 by forming through-holes in the support elements, a dimensional ratio (de/cf) is set to the range of 1–2, where (c) is a cross sectional area of a first through-hole formed as a diffusion limiting inlet (19), (d) is a length of the first through-hole, (e) is a cross sectional area of a second through-hole formed as a diffusion limiting outlet (21) and (f) is a length of the second through-hole.

The diffusion resistance ratio (a/b) between the diffusion resistance of the diffusion-limiting inlet (19) and the diffusion resistance of the diffusion-limiting outlet (21) can be confirmed by measuring two limiting currents of the hydrogen sensor placed in a gas having a predetermined hydrogen concentration, since the limiting current is proportionally dependent on the reciprocal of the diffusion resistance. A first limiting current limited by the diffusion resistance of the diffusion limiting inlet (19) is determined by applying a predeternmined dc voltage across the first and second electrodes (3, 5) as shown in FIG.1, and the second limiting current limited by the diffusion resistance of the diffusion limiting outlet (21) is determined by reversing the polarity of the dc voltage. The diffusion resistance ratio (a/b) is, therefore, identified by the second limiting current divided by the first limiting current.

Figure 1:
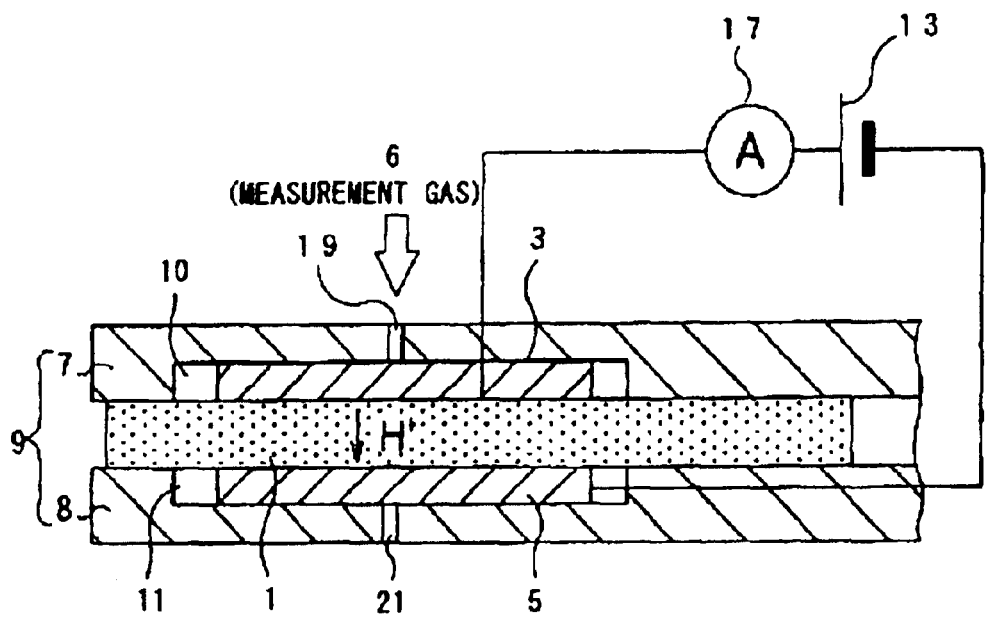
FIG. 1 is an explanatory cutaway view showing a hydrogen sensor of Embodiment 1 of the present invention.

DESCRIPTION OF REFERENCE NUMERALS IN THE DRAWINGS 1, 31 . . . proton conductive layer
3, 33 . . . first electrode
5, 35 . . . second electrode
6, . . . gas atmosphere for measurement
7, 38 . . . first support element
8, 39 . . . second support element
19, 49 . . . gas diffusion limiting inlet
21, 51 . . . gas diffusion limiting outlet
37 . . . reference electrode

DETAILED DESCRIPTION OF THE INVENTION

The present invention will now be explained in greater detail by reference to the drawings. However, the present invention should not be construed as being limited thereto.
Embodiment 1

Referring now to FIG. 1 that is a sectional view of an example hydrogen sensor taken along the longitudinal direction thereof, the hydrogen sensor as shown comprises a proton conductive layer 1 made of a polymer electrolyte; a first electrode 3 and a second electrodes 5 provided on the proton conductive layer 1; a gas diffusion limiting inlet 19 disposed between the first electrode 3, and a measurement gas 6 containing hydrogen to be measured; and a gas diffusion limiting outlet 21 disposed between the second electrode 5 and the measurement gas 6. The first electrode 3 is provided on one surface (upper surface in FIG. 1) of the proton conductive layer 1; the second electrode 5 is provided on the other surface (lower surface in FIG. 1) of the proton conductive layer 1 opposite the first electrode 3; and these components are supported in a support element 9 consisting of a first support element 7 and a second support element 8.

Specifically, the proton conductive layer 1 is held between the first support element 7 and the second support element 8; the first electrode 3 is covered by the first support element 7 while being disposed within a first recess 10; and the second electrode 5 is covered by the second support element 8 while being disposed within a second recess 11.

The hydrogen sensor can be formed into a unitary body as follows: while the proton conductive layer 1 is held between the first support element 7 and the second support element 8, the resultant assembly is fixed by means of a fixing member, a resin adhesive or the like.

The proton conductive layer 1 is formed from a polymer electrolyte and can move protons (H$^+$) from one side thereof to the other side thereof; for example, from the first electrode 3 to the second electrode 5. Preferably, the material of the proton conductive layer 1 allows operation at relatively low temperature (e.g., 150° C. or lower). An example of such a polymer electrolyte material is NAFION (trade name, product of DuPont), which is a fluorine-containing resin.

The first electrode 3 and second electrode 5 are, for example, elastic, porous electrodes that contain a predominant amount of carbon. Each of the first electrode 3 and second electrode 5 is coated with, for example, platinum on the side that contacts the proton conductive layer 1. The platinum coating serves as a catalyst layer.

The first electrode 3 and the second electrode 5 are connected to a circuit via corresponding lead portions such that a power supply cell 13 applies a voltage between the first electrode 3 and the second electrode 5, and the current which flows between the first electrode 3 and the second electrode 5 is measured by means of an ammeter 17. A hydrogen gas contained in the atmosphere is introduced via the diffusion limiting inlet 19 to the first electrode and is caused to be dissociated, decomposed, or reacted by applying a voltage across the first electrode 3 and the second electrode 5 to thereby generate protons at a boundary face between the proton conductive layer 1 and the first electrode 3. The concentration of the hydrogen gas is measured on the basis of a limiting current that is produced by the protons being pumped via the proton conductive layer 1 from the first electrode 3 to the second electrode 5.

The support element 9 is an insulator formed from, for example, ceramic which contains a predominant amount of alumina. In addition to an inorganic insulator formed from, for example, ceramic, an organic insulator formed from, for example, resin can also serve as the support element 9.

The first support element 7, which partially constitutes the support element 9, has a gas diffusion-limiting inlet 19 for establishing communication between an ambient atmosphere (that is a measurement gas atmosphere 6) and the first electrode encapsulated inside the recess 10. The diffusion-limiting inlet 19 is a small aperture (e.g., a through-hole having a circular cross section) adapted to introduce to the side toward the first electrode 3 the measurement gas that may be a fuel gas containing hydrogen therein, and to control diffusion of the gas.

The degree of limiting diffusion can be adjusted by adjusting the inside hole diameter of the diffusion limiting inlet 19 or by filling the diffusion limiting inlet 19 with a porous material such as alumina.

The second support element 8 having the same thickness as that of the first support element 7 has an aperture (e.g., a through-hole having a circular cross section) therein for establishing communication between the ambient atmosphere and the second electrode encapsulated inside the recess 11. The hole serves as the gas diffusion-limiting outlet 21.

Particularly, in the present embodiment, the size (0.003 mm$^2$ cross-sectional area×1.6 mm length) of the diffusion-limiting inlet 19 and the size (0.005 mm$^2$ cross-sectional area×1.6 mm length) of the gas diffusion-limiting outlet 21 are determined such that the ratio (a/b) between the diffusion resistance (a) of the diffusion limiting-inlet 19 and the diffusion resistance (b) of the gas diffusion- limiting outlet 21 is not greater than 2.

Notably, the diffusion resistance mentioned above is a value indicative of difficulty in diffusion of gas. When the diffusion-limiting inlet and the diffusion-limiting outlet assume the form of, for example, a through-hole, the diffusion resistance thereof is proportional to the length of the hole and inversely proportional to cross-sectional area of the hole. Therefore, the diffusion resistance can be adjusted by adjusting the size of the through-hole. In the case where the through-hole is filled with a porous material, the diffusion resistance can be adjusted by adjusting, for example, porosity or pore size of the material.

On the other hand, the ratio (a/b) of the diffusion resistance (a) of the gas diffusion-limiting inlet (19) to the gas diffusion-limiting outlet 21 can be easily confirmed by measuring two limiting currents of the hydrogen sensor placed in a gas atmosphere having a predetermined constant hydrogen concentration (for example, of 50% hydrogen concentration), as explained below. A first limiting current that inversely corresponds to the diffusion resistance of the gas diffusion-limiting inlet 19 is determined by measuring the current that flows between the first and second electrodes 3,5 under a constant dc voltage of, for instance, 200 mV being applied across the first and second electrodes 3,5. A second limiting current that inversely corresponds to the gas diffusion resistance of the gas diffusion-limiting outlet 21 is determined by measuring the current that flows between the first and second electrodes 3,5 under the same constant dc voltage with reversed polarity being applied across the first and second electrodes 3,5. As the limiting current is proportionally dependent on the reciprocal of the diffusion resistance, the diffusion resistance ratio (a/b) can be identified by the second limiting current divided by the first limiting current.

Next will be described the principle of measurement and the procedure of measurement with respect to the hydrogen sensor of the present embodiment. When the hydrogen sensor is exposed to a fuel gas containing hydrogen, the hydrogen that has reached the first electrode 3 from the ambient atmosphere 6 via the diffusion limiting inlet 19 induces an electromotive force between the first electrode 3 and the second electrode 5 via the proton conductive layer 1, the electromotive force depending on the difference in hydrogen concentration between the first electrode 3 and the second electrode 5.

Then, a power supply cell 13 applies a dc voltage between the first electrode 3 and the second electrode 5. As a result, hydrogen is dissociated into protons on the first electrode 3; the thus-generated protons are pumped out to the second electrode 5 via the proton conductive layer 1 to become hydrogen again; and the thus-generated hydrogen diffuses via the diffusion-limiting outlet 21 into the atmosphere 6 outside the sensor.

At this time, as the current flowing between the first electrode 3 and the second electrode 5 (i.e., a limiting current represented by the upper limit current reachable upon application of the aforementioned constant voltage) becomes proportional to the hydrogen gas concentration, measurement of this limiting current enables determination of hydrogen gas concentration of the measurement gas.

Next, a method for manufacturing the hydrogen sensor of the present embodiment will be briefly described. For example, as shown in FIG. 1, the second support element 8 is placed on a bench with the second recess 11 thereof facing upward. Then, the proton conductive layer 1 with the first electrode 3 and the second electrode 5 being disposed on the corresponding opposite sides thereof is placed on the second support element 8 such that the second electrode 5 is accommodated in the second recess 11. Thereafter, the first support element 7 is disposed on the proton conductive layer 1 such that the first electrode 3 is encapsulated inside the first recess 10. In this state that the proton conductive layer I is held between the first support element 7 and the second support element 8, the resultant assembly is press-fixed in the thickness direction thereof (in the vertical direction in FIG. 1) by means of a fixing member or the like, thereby yielding a hydrogen sensor.

Notably, the side faces of the hydrogen sensor are covered with, for example, a resin adhesive so as to seal the sensor except for the diffusion limiting inlet 19, whereby introduction of hydrogen gas is allowed only through the diffusion limiting portion 19.

Next, advantages yielded by the hydrogen sensor of the present embodiment will be described. The hydrogen sensor assumes a ratio (a/b) between the diffusion resistance (a) of the diffusion limiting portion 19 and the diffusion resistance (b) of the gas outlet portion 21 of not greater than 2, or preferably in the range of 1–2. Thus, even during transition when the concentration of hydrogen gas in a fuel gas for use in a polymer electrolyte fuel cell increases abruptly, the amount of hydrogen gas which reaches the second electrode 5 through the gas diffusion-limiting outlet 21 is not very large as compared with that of the hydrogen gas which reaches the first electrode 3 through the diffusion limiting inlet.

Figure 2:
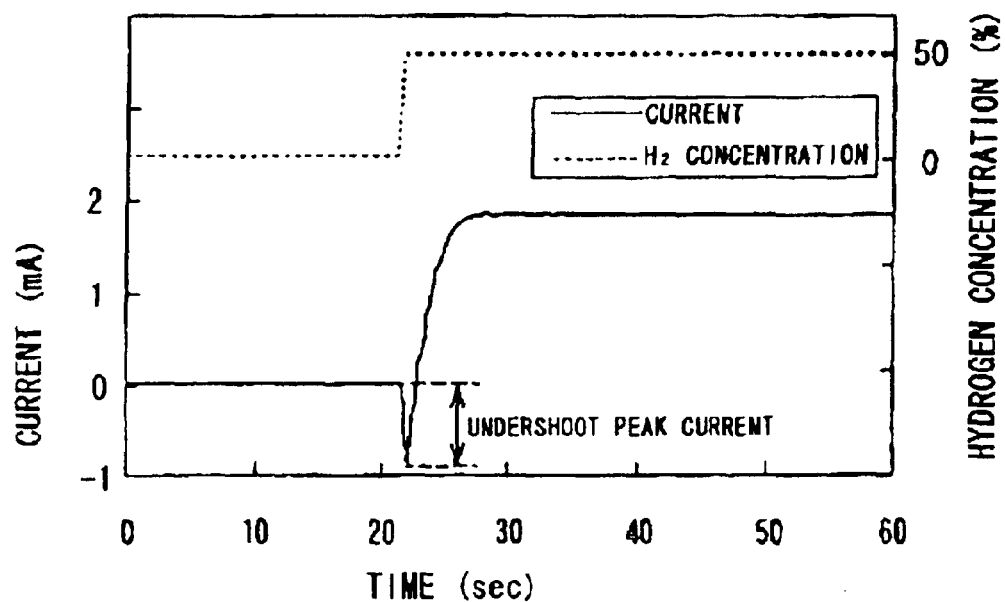
FIG. 2 is a graph showing a current output profile of a hydrogen gas sensor of a Comparative Example.

Therefore, the generation of unusual hydrogen sensor output;

specifically, the generation of unusual electromotive force that induces undershoot current as shown in FIG. 2, can be effectively or completely suppressed, whereby, even during transition, accurate measurement of hydrogen gas concentration can be accomplished.

Next, an experiment which was carried out in order to verify the advantages of the embodiment will be described. This experiment evaluated hydrogen sensor output (specifically current flowing between the first electrode and the second electrode) while the diffusion resistance of the diffusion limiting inlet and that of the gas diffusion outlet were varied.

(1) First will be described a hydrogen sensor (Comparative Example) that involves generation of undesirable undershooting current, which falls outside the scope of the present invention. A hydrogen sensor was manufactured having a diffusion resistance ratio (a/b) of 10 between the diffusion resistance (a) of the diffusion limiting inlet and the diffusion resistance (b) of the diffusion limiting outlet. Other features were made similar to those of Embodiment 1. Specifically, the cross-sectional area of the through-hole formed as the diffusion-limiting inlet was 0.003 mm$^2$, and the cross-sectional area of the through-hole formed as the diffusion-limiting outlet was 0.03 mm$^2$. Since diffusion resistance is inversely proportional to cross-sectional area, the diffusion resistance ratio a/b is calculated as (1/0.003)/(0.03)=10.

By use of the above-described hydrogen sensor (Comparative Example), hydrogen gas concentration was measured. Specifically, in the course of abruptly increasing the concentration of hydrogen contained in a measurement gas, the current flowing between the first electrode and the second electrode was measured.

Measuring conditions are itemized below.

<Measuring conditions>

Gas composition: $H_2=0 \rightarrow 50\%$, $H_2O=20\%$, $N_2$=bal.

Gas temperature: 80° C.

Gas flow rate: 10 L/min

Voltage applied between two electrodes: 200 mV (dc)

Measurement results are shown in FIG. 2 that is a graph in which the vertical axis represents current, and the horizontal axis represents elapsed time.

As is apparent from FIG. 2, this hydrogen sensor (Comparative Example) generated significant undershooting current, upon abrupt increase in hydrogen gas concentration, which is undesirable for measurement.

(2) Next, seven kinds of hydrogen sensors were manufactured in a manner similar to that of Embodiment 1, except that the diffusion resistance ratio (a/b) was set to 1, 1.7, 2, 2.3, 2.8, 3.6 and 4, respectively. In the course of abruptly increasing hydrogen concentration, as in the case of Comparative Example (1), the current flowing between the first electrode and the second electrode was measured. Measurement results are shown in a graph in FIG. 3, in which the vertical axis represents peak value of undershooting current as referred to FIG. 2, and the horizontal axis represents the diffusion resistance ratio (a/b).

Figure 3:
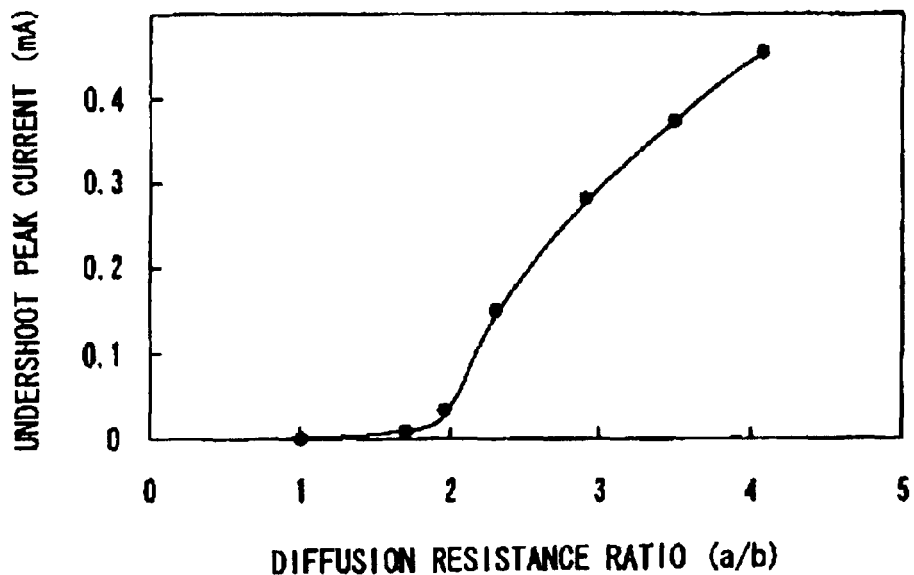
FIG. 3 is a graph showing a profile of undershooting current peak in relation to diffusion resistance ratio a/b.

As seen from FIG. 3, the hydrogen sensors having a diffusion resistance ratio (a/b) not greater than 2 are substantially free from undershooting current, thereby proving capability of accurately detecting hydrogen gas concentration during transition. By contrast, when a diffusion resistance ratio (a/b) exceeds 2, an abrupt increase in undershooting current occurs, causing undesirable measurement confusion. Notably, if the ratio is far less than 1 such as 0.3, the response speed of the output current is affected. A practical range of the diffusion resistance ratio (a/b) is preferably 1–2.

Embodiment 2

Embodiment 2 will next be described. However, repeated description of features similar to those of Embodiment 1 will be omitted. The hydrogen sensor of this embodiment 2 assumes a configuration similar to Embodiment 1 except that a reference electrode is added.

Figure 4:
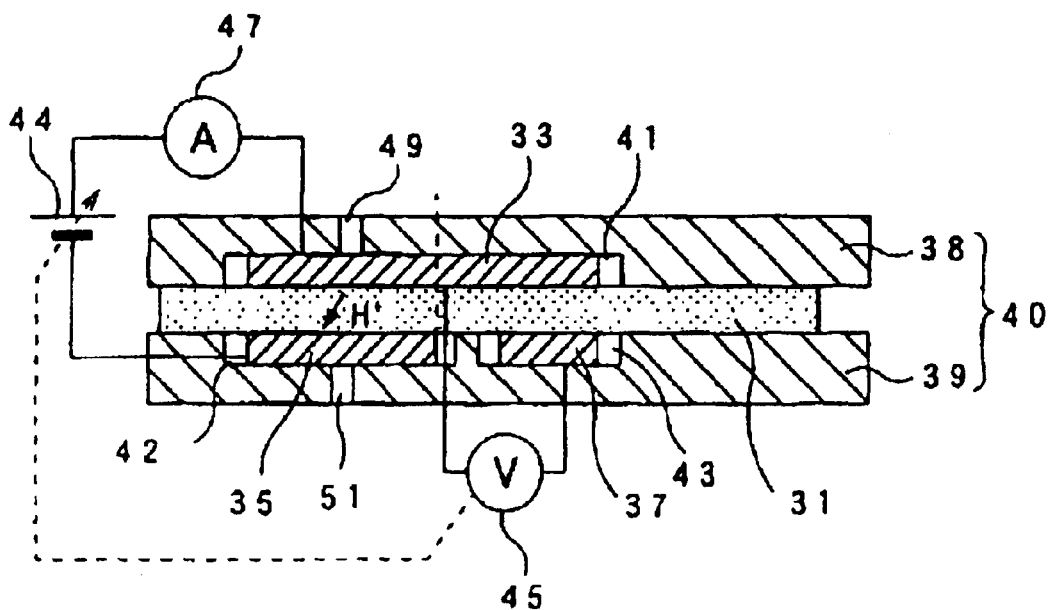
FIG. 4 is an explanatory cutaway view showing a hydrogen sensor of Embodiment 2 of the present invention.
Figure 5:
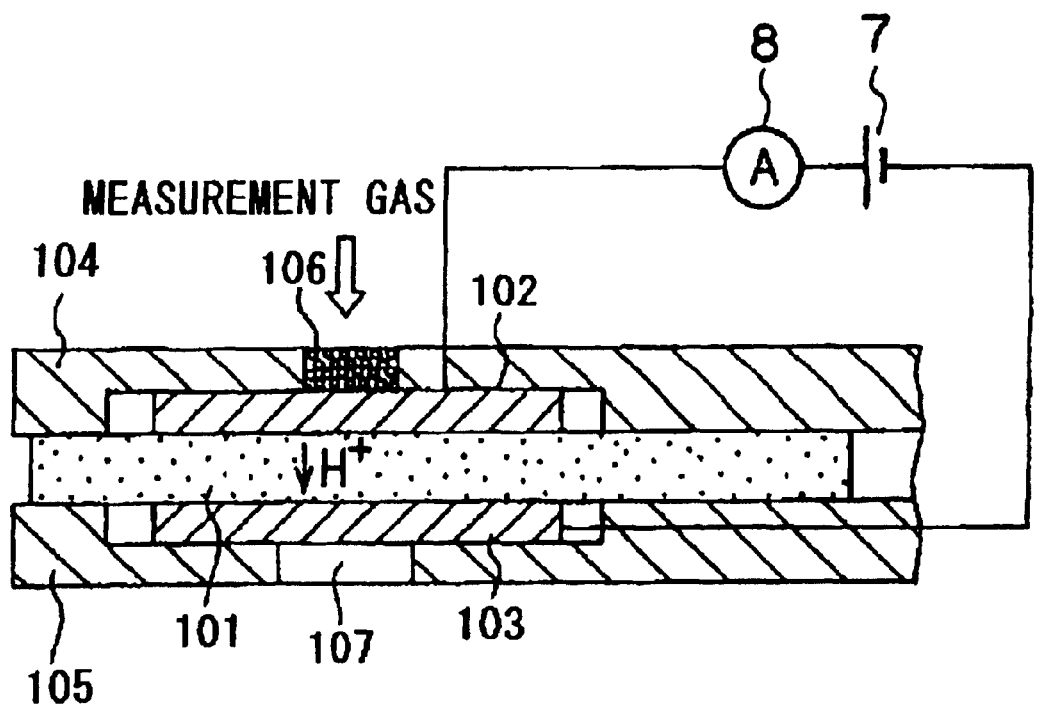
FIG. 5 is an explanatory cutaway view showing a conventional hydrogen sensor.

As shown in FIG. 4 that is a sectional view of the hydrogen sensor taken along the longitudinal direction thereof, the hydrogen sensor is configured such that a first electrode 33 is provided on a surface of a proton conductive layer 31; a second electrode 35 and a reference electrode 37 are provided on the other surface of the proton conductive layer 31 in opposition to the first electrode 33; and these components are supported in a support element 40 consisting of a first support element 38 and a second support element 39.

Specifically, the proton conductive layer 31 is held between the first support element 38 and the second support element 39; the first electrode 33 is covered by the first support element 38 while being encapsulated within a first recess 41; the second electrode 35 is covered by the second support element 39 while being encapsulated within a second recess 42; and the reference electrode 37 is covered by the second support element 39 while encapsulated within a third recess 43.

The proton conductive layer 31 is formed from a polymer electrolyte made of NAFION (product of DuPont) and can move protons ($H^+$) from one side thereof to the other side thereof; for example, from the first electrode 33 to the second electrode 35. The first electrode 33, the second electrode 35, and the reference electrode 37 are, for example, porous electrodes containing a predominant amount of carbon. Each of the electrodes 33, 35, and 37 is coated with, for example, platinum on the side that comes into contact with the proton conductive layer 31. The platinum coating serves as a catalyst layer.

The first electrode 33, the second electrode 35, and the reference electrode 37 are connected to a circuit via corresponding lead portions such that a power supply cell 44 applies a voltage between the first electrode 33 and the second electrode 35; the voltage produced between the first electrode 33 and the reference electrode 37 is measured by means of a voltmeter 45; and the current which flows between the first electrode 33 and the second electrode 35 is measured by means of an ammeter 47.

The reference electrode 37 is used because measurement of the hydrogen concentration of the measurement gas on a basis of the current flowing the first and second electrodes 33,35 is not affected by disturbances caused by temperature or humidity variation, when a constant voltage is applied across the first electrode 33 and the reference electrode 37. In order to stabilize hydrogen concentration on the reference electrode 37, a hydrogen self-generating type of the reference electrode is advantageously used. This mechanism of hydrogen self-generation by the reference electrode 37 is attained by flowing a small constant current (e.g., 10 $\mu$A) from the first electrode 33 to the reference electrode 37. As a result a reference atmosphere with a constant hydrogen concentration is formed inside the third recess 43 that encapsulates the reference electrode 37.

The support element 40 is an insulator formed from, for example, ceramic which contains a predominant amount of alumina. The first support element 38, which partially constitutes the support element 40, has a through hole that serves as a gas diffusion-limiting inlet 49 for establishing communication between an ambient atmosphere and the first recess 41. The second support element 39 has a through-hole that serves as a gas-diffusion outlet 51 for establishing communication between the ambient atmosphere and the second recess 11.

Also, in this Embodiment 2, the size of the diffusion limiting inlet 49 and the size of the diffusion-limiting outlet 51 are advantageously determined such that the resistance ratio (a/b) between the diffusion resistance (a) of the diffusion-limiting inlet 49 and the diffusion resistance (b) of the diffusion-limiting outlet 51 is not greater than 2, or preferably in the range of 1–2.

Next, the principle of measurement and the procedure of measurement with respect to the hydrogen sensor of Embodiment 2 will be described. When the hydrogen sensor is exposed to measurement gas such as a fuel gas containing hydrogen, the hydrogen which has reached the first electrode 33 from an ambient atmosphere (namely, the measurement gas such as the fuel gas) via the diffusion limiting inlet 49 causes an electromotive force across the first electrode 33 and the reference electrode 37 via the proton conductive layer 31 as a function of the difference in hydrogen gas concentration between the first electrode 33 and the reference electrode 37.

The power supply cell 44 applies an appropriate voltage of for instance 180–400 mV between the first electrode 33 and the second electrode 35 such that an electrical potential difference between the first electrode 33 and the reference electrode 37 becomes constant. In other words, hydrogen gas concentration on the first electrode 33 is controlled at a constant level by varying the voltage that is applied across the first electrode 33 and the second electrode 35 to an optimum level. For example, when the concentration of hydrogen gas in the fuel gas is high, the voltage applied between the first electrode 33 and the second electrode 35 is increased; and when the hydrogen gas concentration is low, the voltage is decreased. As another example, when variation of the temperature of the fuel gas causes an increase in resistance between the first electrode 33 and the second electrode 35, the applied voltage is varied appropriately so as to control hydrogen gas concentration on the first electrode 33 at a constant level.

As a result, hydrogen is stably dissociated into protons on the first electrode 33; the thus-generated protons are pumped out via the proton conductive layer 31 to the second electrode 35 to recompose the protons into hydrogen; and the thus-recomposed hydrogen diffuses out into the atmosphere. At this time, since current flowing between the first electrode 33 and the second electrode 35 (namely, a limiting current that is an upper limit current reachable upon application of the aforementioned voltage) is proportional to hydrogen gas concentration, measurement of the current enables determination of hydrogen concentration of the measurement gas.

Particularly, by setting the electrical potential difference between the first electrode 33 and the reference electrode 37 to an optimum constant value, even in application to a gas atmosphere involving great variation caused by, for example, temperature, the hydrogen gas concentration on the first electrode 33 can always be adjusted to an optimum valve, whereby hydrogen gas concentration can be measured at higher accuracy (as compared to a hydrogen sensor wherein the reference electrode 37 is not employed).

The advantage of the hydrogen sensor of Embodiment 2 will be described. As in the sensor of Embodiment 1, the ratio (a/b) between the diffusion resistance (a) of the diffusion limiting portion 49 and the diffusion resistance (b) of the gas outlet portion 51 is not greater than 2,or preferably in the range of 1–2, whereby hydrogen gas concentration can be measured accurately and speedily.

Particularly, since the sensor in Embodiment 2 employs the reference electrode 37, measurement of hydrogen gas concentration is attained at higher accuracy and with higher reliability.

The present invention is not limited to the above-described Embodiments, but may be embodied in many other specific forms without departing from the spirit or scope of the invention. For example, Embodiments 1 and 2 are described with reference to a hydrogen sensor for measuring the concentration of hydrogen contained in a measurement gas such as a fuel gas. The present invention may be applicable to measurement of concentration of other gases such as carbon monoxide and methanol gas contained in the hydrogen-containing gas.

This application is based on Japanese Patent Application No. 2001-344780 filed Nov. 9, 2001, the disclosure of which is incorporated herein by reference in its entirety.

What is claimed is:

1. A gas sensor comprising:

a proton conductive layer;

a first electrode and a second electrode provided on the proton conductive layer;

a gas diffusion-limiting inlet provided between the first electrode and a measurement gas atmosphere containing a hydrogen gas;

and a gas diffusion-limiting outlet provided between the second electrode and the atmosphere, wherein a diffusion ratio (a/b) between diffusion resistance (a) of the diffusion limiting inlet and diffusion resistance (b) of the diffusion limiting outlet is in the range of about 1–2.

2. The gas sensor as claimed in claim 1, further comprising a reference electrode that is disposed on the proton conductive layer;

wherein concentration of the hydrogen gas component is measured on the basis of the limiting current flowing across the first electrode and the second electrode by maintaining a constant electrical potential difference between the first electrode and the reference electrode and by varying the voltage applied across the first electrode and the second electrode.

3. The gas sensor as claimed in claim 1, wherein the proton conductive layer is made of a polymer electrolyte that transports protons at a temperature of less than 150° C.

4. The gas sensor as claimed in claim 3, wherein the polymer electrolyte comprises a fluorine-containing resin.

5. The gas sensor as claimed in claim 1, wherein said gas diffusion-limiting inlet comprises a first through-hole and said gas diffusion-limiting outlet comprises a second through-hole, and wherein the diffusion resistance ratio (a/b) falls in the range of 1–2 when a dimensional ratio (de/cf) is set to fall in the range of 1–2, where (c) is a cross sectional area of the first through-hole, (d) is the length of the first through-hole, (e) is a cross sectional area of the second through-hole, and (f) is the length of the second through-hole.

6. The gas sensor as claimed in claim 1, wherein the diffusion resistance ratio (a/b) is identified by a second limiting current divided by the first limiting current, said second limiting current being determined by reversing a polarity of the voltage applied across the first electrode and second electrode to determine the first limiting current.

7. The gas sensor as claimed in claim 1, wherein the gas sensor is a hydrogen sensor for measuring the concentration of hydrogen gas contained in a measurement gas, and wherein hydrogen gas contained in the measurement gas is introduced via the gas diffusion-limiting inlet to the first electrode and is caused to be dissociated, decomposed, or reacted by applying a voltage across the first electrode and the second electrode to thereby generate protons at a boundary interface between the proton conductive layer and the first electrode, and the concentration of hydrogen gas is measured on the basis of a limiting current that is generated by protons being pumped via the proton conductive layer from the first electrode to the second electrode.

8. The gas sensor as claimed in claim 1, wherein the gas sensor is a hydrogen sensor for detecting hydrogen concentration of a fuel gas for use in a polymer electrolyte fuel cell.

* * * * *